(12) United States Patent
Docherty et al.

(10) Patent No.: US 6,915,154 B1
(45) Date of Patent: Jul. 5, 2005

(54) METHOD AND APPARATUS FOR PERFORMING INTRA-OPERATIVE ANGIOGRAPHY

(75) Inventors: John C. Docherty, Winnipeg (CA); Mark Hewko, Winnipeg (CA); Gurpreet Mangat, Richmond Hill (CA); Robert W. Flower, Hunt Valley, MD (US); Seshadri M. Chari, Toronto (CA)

(73) Assignee: National Research Council of Canada, Ontario (CA)

( * ) Notice: Subject to any disclaimer, the term of this patent is extended or adjusted under 35 U.S.C. 154(b) by 355 days.

(21) Appl. No.: 09/744,034

(22) PCT Filed: Aug. 11, 2000

(86) PCT No.: PCT/US00/22088

§ 371 (c)(1),
(2), (4) Date: Apr. 27, 2001

(87) PCT Pub. No.: WO01/22870

PCT Pub. Date: Apr. 5, 2001

Related U.S. Application Data

(60) Provisional application No. 60/155,652, filed on Sep. 24, 1999.

(51) Int. Cl.⁷ .............................. A61B 6/00; A61B 5/05
(52) U.S. Cl. ....................................... 600/431; 600/419
(58) Field of Search ................................ 600/431, 432, 600/433, 434, 435, 407, 300, 419, 312–317, 476, 473; 250/302; 424/9.6, 9.61; 351/206, 205, 208

(56) References Cited

U.S. PATENT DOCUMENTS

| | | | |
|---|---|---|---|
| 4,619,249 A | 10/1986 | Landry | |
| 4,995,396 A * | 2/1991 | Inaba et al. | 600/431 |
| 5,375,603 A * | 12/1994 | Feiler | 600/474 |
| 5,394,199 A | 2/1995 | Flower | |
| 5,437,274 A | 8/1995 | Khoobehi et al. | |
| 5,507,287 A | 4/1996 | Palcic et al. | |
| 5,785,965 A * | 7/1998 | Pratt et al. | 424/93.21 |
| 5,927,284 A * | 7/1999 | Borst et al. | 128/898 |
| 5,951,980 A * | 9/1999 | Collen | 424/94.64 |
| 6,122,042 A | 9/2000 | Wunderman et al. | |
| 6,246,901 B1 * | 6/2001 | Benaron | 600/431 |
| 6,280,386 B1 * | 8/2001 | Alfano et al. | 600/431 |
| 6,351,663 B1 * | 2/2002 | Flower et al. | 600/476 |
| 6,447,443 B1 * | 9/2002 | Keogh et al. | 600/37 |
| 6,498,945 B1 * | 12/2002 | Alfheim et al. | 600/407 |

FOREIGN PATENT DOCUMENTS

| | | |
|---|---|---|
| CA | 2212257 A1 | 8/1996 |
| CA | 2413033 A1 | 3/2000 |
| CN | 1200174 | 11/1998 |
| WO | WO97/08538 A1 | 3/1997 |
| WO | WO98/30144 A1 | 7/1998 |
| WO | WO01/17561 A1 | 3/2001 |

OTHER PUBLICATIONS

Laub, G.W. et al., "Experimental Use of Fluorescein for Visualization of Coronary Arteries," *Vascular Surgery*, vol. 23, No. 6, pp. 454–457; 1989.

(Continued)

*Primary Examiner*—Daniel Robinson
(74) *Attorney, Agent, or Firm*—Kudirka & Jobse LLP

(57) ABSTRACT

Method for assessing the patency of a patient's blood vessel, advantageously during or after treatment of that vessel by an invasive procedure, comprising administering a fluorescent dye to the patient; obtaining at least one angiographic image of the vessel portion; and evaluating the at least one angiographic image to assess the patency of the vessel portion. Other related methods are contemplated, including methods for assessing perfusion in selected body tissue, methods for evaluating the potential of vessels for use in creation of AV fistulas, methods for determining the diameter of a vessel, and methods for locating a vessel located below the surface of a tissue.

11 Claims, 1 Drawing Sheet

OTHER PUBLICATIONS

Rubben, A. et al., "Infrared Videoangiofluorography of the Skin with Indocyanine Green–Rat Random Cutaneous Flap Model and Results in Man," *Microvascular Research*, vol. 47, No. 2, pp. 240–250; Mar. 1994.

Lee, E.T. et al., "A New Method for Assessment of Changes in Retinal Blood Flow," *Medical Engineering & Physics*, vol. 19, No. 2, pp. 125–130; Mar. 1997.

Lund, F. et al., "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs," *Clinical Physiology*, vol. 17, No. 6, pp. 619–633; Nov. 1997.

Taylor, Kenneth M., "Brain Damage During Cardiopulmonary Bypass," *Annals of Thoracic Surgery*, vol. 65, No. 4 suppl., pp. S20–S26; Apr. 1998.

Wollert, H.G. et al., "Intraoperative Visualization of Coronary Artery Fistula Using Medical Dye," *The Thoracic and Cardiovascular Surgeon*, vol. 46, No. 6, pp. 382–383; Dec. 1998.

Still, Joseph et al., "Evaluation of the Circulation of Reconstructive Flaps Using Laser–Induced Fluorescence of Indocyanine Green," *Annals of Plastic Surgery*, vol. 42, No. 42, pp. 266–274; 1999.

Supplementary European Search Report (Jun. 22, 2004).

* cited by examiner

METHOD AND APPARATUS FOR PERFORMING INTRA-OPERATIVE ANGIOGRAPHY

CROSS-REFERENCE TO RELATED PATENT APPLICATIONS

This patent application claims the benefit of U.S. provisional patent application No. 60/155,652, filed Sep. 24, 1999.

TECHNICAL FIELD OF THE INVENTION

This invention generally pertains to procedures for observing blood flow through the cardiovascular system of an animal.

BACKGROUND OF THE INVENTION

Disease and injury affecting the cardiovascular system in animals, and particularly humans, are commonplace in today's society. One such disease is atherosclerosis. This disease is characterized by partial blockage (stenosis) of a blood vessel, typically by a narrowing of one or more arteries. In its most severe form, the vessel narrows to the point that it becomes completely blocked (occluded). In coronary arteries, stenosis and occlusion often manifest themselves in the form of severe chest pains and, potentially, myocardial infarction (heart attack). Not limited to coronary arteries, atherosclerosis can also affect the peripheral vasculature, i.e., arteries (and veins) that circulate blood throughout the arms and legs, the carotid arteries, i.e., arteries that carry blood to the brain, and intracranial arteries, i.e., arteries that distribute blood within the brain.

One therapy commonly employed in an effort to overcome the effects of atherosclerosis in coronary and peripheral vessels is bypass graft surgery. During this procedure, a vascular graft, e.g., a vein or artery or, alternatively, a flexible artificial tube, is surgically inserted in a manner that permits blood to bypass the stenotic or occluded portion of a native vessel. Perhaps the best-known example of bypass graft surgery is coronary artery bypass graft (CABG) surgery. In CABG, a graft, commonly a saphenous vein or internal mammary artery, is harvested or dissected from the patient, respectively, and then located within the patient to permit blood flow to bypass the stenotic or occluded vessel portion. Alternatively, or in addition thereto, a graft may be used to permit blood to flow directly from the aorta to a location downstream of a stenotic or occluded portion of an artery.

The success of bypass grafts, at least in terms of clinical improvement, depends in significant part upon the ability of the treated vessel to remain free of occlusions over both the short- and long-term. This freedom from occlusions is commonly referred to as vessel patency. Poor patency in the first few months after surgery is thought to be the result of various factors, with the following believed to be the most significant: poor blood circulation, poor coronary arterial runoff, injury to the graft during preparation or faulty surgical technique.

While cardiac surgery in recent years has focused on strategies to minimize trauma to the myocardium, these strategies may increase the likelihood of problems if used during vessel grafting procedures. For example, while surgical techniques now permit CABG to be performed on a beating heart to minimize trauma, there exists a concern relating to the quality of the resulting graft. The use of limited access incisions during CABG procedures has been developed for, at least, the revascularization of the left anterior descending artery using a left internal mammary artery, with the hope of faster recovery, a shorter hospital stay and reduction in cost. However, this method has also raised concerns relating to graft quality. Indeed, there exist reports of early failure in grafts completed using limited access incisions.

Other issues affecting CABG procedures are diagnostic in nature, and include relatively slow and inaccurate identification of stenotic and occluded vessels during the initial phase of CABG procedures (as some of these vessels lie within the heart tissue which inhibits visual identification), and an inability to quickly and accurately determine the extent of blood flow through the relatively smaller downstream vessels (and, more generally, whether the graft was successful in restoring blood flow to affected tissue) after the graft is completed.

Arterial patency issues may arise in therapies that do not include grafts. For example, patency evaluation is desirable in carotid arteries during and after an endarterectomy, in cranial vessels during and after neurosurgery, and in the context of kidney hemodialysis, wherein an assessment of AV fistula patency is desirable. While vessel patency information in these contexts may be obtained using X-ray technology, the disadvantages mentioned previously remain.

The extent of blood flow within a particular tissue or portion thereof, commonly referred to as perfusion, is important in connection with the diagnosis and treatment of a variety of ailments. For example, a perfusion analysis would be desirable in the context of a treatment designed to reduce undesired blood flow into tissue, e.g., halting blood flow into a tumor. At present, MRI may be used to obtain perfusion information, but this information is imprecise and only available after treatment is completed. This lessens the probability that a physician will be able to identify and remedy problems during that same procedure, thereby precluding the need for a subsequent remedial procedure.

Another affliction that requires treatment of the circulatory system is renal failure. In many cases of renal failure, it is desirable to create an AV fistula to provide vascular access for hemodialysis. The fistula is created by joining an artery and vein by a surgical procedure, providing a vessel having a relatively high rate of blood flow. While X-ray technology can be used to assist the physician in determining whether the creation of a properly functioning fistula is possible, and the type of fistula that should be created, the technology suffers from the previously mentioned limitations.

In view of the foregoing, a need exists for a diagnostic procedure that permits a physician to evaluate the patency of a particular vessel, and particularly vessels that have undergone an invasive procedure such as a bypass graft procedure. A further need exists for a method of quickly and accurately locating a particular stenotic or occluded vessel, such as a coronary artery during the initial phase of CABG surgery. In addition, improved methods for evaluating the extent of blood flow downstream of a graft are needed, e.g., in coronary arteries and peripheral vasculature, as are more accurate methods for determining the extent of blood perfusion in selected body tissue. A need also exists for an improved means of identifying candidate vessels for AV fistulas, and of obtaining information relevant to a determination of the type of fistula that should be created in a patient with renal impairment.

BRIEF SUMMARY OF THE INVENTION

The present invention meets the forgoing and other needs by providing, in one aspect, a method for assessing the patency of an animal's blood vessel, advantageously during an invasive procedure in which the vessel is treated. The method comprises the steps of administering a fluorescent dye to the animal; obtaining at least one angiographic image of the vessel portion; and evaluating the at least one angiographic image to assess the patency of the vessel portion.

A related aspect provides for assessing blood flow in a portion of tissue in an animal wherein the tissue is a candidate for an invasive procedure, is undergoing an invasive procedure, or has undergone such a procedure, comprising identifying the tissue portion in the animal; administering a fluorescent dye to the animal; obtaining at least one angiographic image of blood flowing through the tissue portion; and examining the at least one angiographic image to assess blood flow in the tissue portion.

A further aspect of the present invention permits a physician to accurately determine the extent to which a selected portion of body tissue, e.g., heart tissue, tumor, is well perfused, to assist in the identification and diagnosis of improperly (or properly) perfused tissue. The method comprises the steps of selecting a portion of body tissue to be analyzed; administering a fluorescent dye to the patient; obtaining at least one angiographic image of the selected tissue; and examining the at least one angiographic image to assess the extent of blood flow within the selected portion of body tissue.

In a related aspect, the present invention provides a method for evaluating chemical agents and other proposed therapies in terms of their effect on vasculature. The method comprises obtaining a first angiographic image of selected vasculature; administering a therapeutic agent; obtaining a second angiographic image of the selected vasculature on a subsequent day; and comparing the first and second angiographic images to determine if there is any change in vascular density over that time period.

In another aspect of the present invention, a method of locating, in an animal, at least one vessel (or portion thereof) residing beneath the surface of vascularized tissue is provided. The method comprises the steps of administering a fluorescent dye to the animal; obtaining at least one angiographic image of the vasculature located beneath the surface of the tissue; and examining the at least one angiographic image to locate the at least one vessel residing beneath the surface of the tissue.

In a further aspect, the present invention provides an apparatus for determining the diameter of a blood vessel. More specifically, the apparatus comprises: a device that emits radiation capable of causing fluorescent dye to fluoresce; a camera capable of capturing the radiation emitted by the fluorescing dye within the blood vessel as an angiographic image comprised of a plurality of pixels; and a computer comprising a software program that calculates the diameter of a blood vessel by comparing the number of pixels that correspond to the blood vessel diameter with the number of pixels associated with a preselected unit of measurement.

These and other features and advantages of the present invention will become apparent upon review of the following figure and detailed description of the preferred embodiments of the present invention.

DETAILED DESCRIPTION OF THE INVENTION

Figure 1:
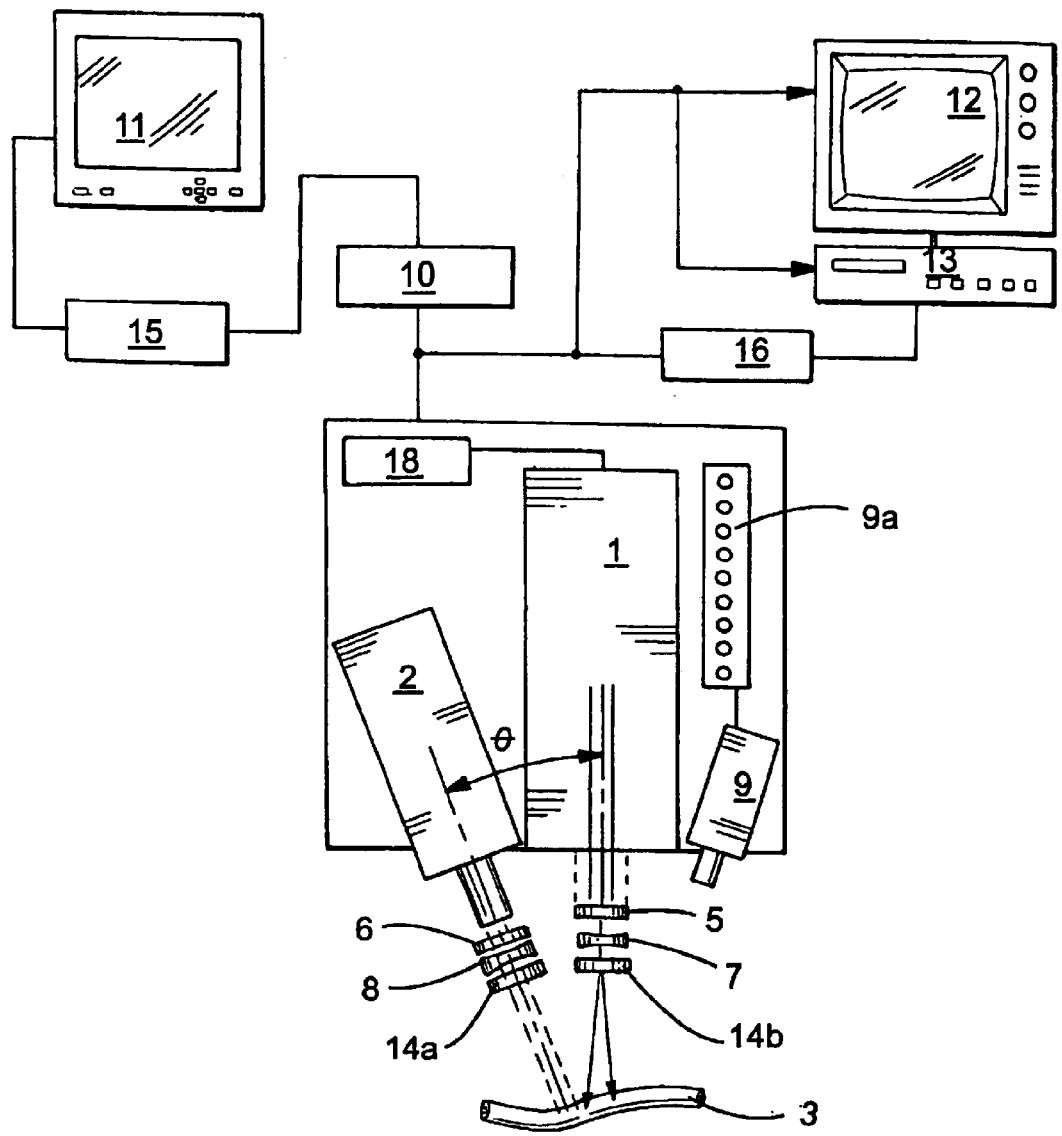
FIG. 1 illustrates in schematic form a preferred embodiment of the apparatus of the present invention.

The methods of the present invention are claimed and described herein as a series of treatment steps. It should be understood that these methods and associated steps may be performed in any logical order. Moreover, the methods may be performed alone, or in conjunction with other diagnostic procedures and treatments administered before, during or after such methods and steps set forth therein without departing from the scope and spirit of the present invention. Further, it is contemplated that the term animals as used herein includes, but is not limited to, humans.

Turning now to one aspect of the present invention, a method is provided for analyzing the patency of a portion of an animal's blood vessel. The method comprises the steps of administering a fluorescent dye to the animal; obtaining at least one angiographic image of the vessel portion; and evaluating the at least one angiographic image to assess the patency of the vessel portion.

Illustrative of the vessels whose patency may be evaluated in accordance with the inventive method include coronary arteries, the peripheral vasculature, carotid arteries, intracranial vessels and AV fistulas. An evaluation of vessel patency may be conducted qualitatively by a visual inspection of the images and, if desired, quantitatively by obtaining a measurement of vessel diameter, wherein a substantially uniform diameter of a particular vessel portion's lumen is desirable.

Advantageously, vessel patency may be determined during an invasive procedure. For purposes of this and other aspects of the present invention, an invasive procedure is one in which one or more incisions are made in the tissue of an animal, or entry of an instrument into an orifice of an animal is undertaken, to diagnose or treat an affliction or condition that directly or indirectly affects vasculature or tissue. The invasive procedure should be understood to continue until the incisions are sutured, or the instrument is withdrawn from the animal, respectively.

By way of example, this aspect of the invention contemplates a physician, during a single invasive procedure, obtaining angiographic images of a coronary artery both prior to and after treatment (e.g., bypass). In this way, the physician is able to quickly evaluate the patency of the treated vessel. This is beneficial because it allows a physician, upon noting a problem in the treated vessel, to take remedial measures during the same invasive procedure, sparing the animal from the trauma associated with a subsequent remedial invasive procedure.

Examples of vessel portions that may benefit from use of the inventive method include, but are not limited to, vessels that have been subjected to: repair (due to injury, aneurysm and/or malformation) or bypass (of coronary arteries or peripheral vasculature); endarterectomies; intracranial surgery; creation of AV fistulas; and surgical procedures conducted using an endoscope or related devices.

Illustrative of the types of repair include, but are not limited to: lacerated vessels closed by suture or adhesive; removal of an aneurysm or other vessel malformation by removing the undesired portion of a vessel followed by either joining the two remaining ends of the vessel to one another, or the interposition and subsequent joining of a natural or synthetic vessel graft to the remaining vessel ends.

Bypass is commonly used when a portion of a blood vessel, typically a stenotic or occluded portion, requires circumvention. Bypass includes, but is not limited to, attaching the ends of a graft vessel at locations upstream and downstream of the stenosis; occlusion or other problem, as well as grafting one end of a relatively healthy artery onto the undesired vessel at a location downstream of the stenosis, occlusion, or other problem. One specific example of the latter is a procedure wherein one end of a healthy artery from the chest wall is grafted onto a coronary artery downstream of a stenotic or occluded portion thereof. The inventive method is preferably utilized in surgery involving the bypass of coronary arteries, e.g., CABG surgery.

When bypass is undertaken, an anastomosis, i.e., the junction of the native and graft vessels, is created. The patency of anastomoses is of particular interest to physicians. In a preferred aspect, the inventive method contemplates the assessment of the patency of anastomoses, more preferably during the invasive procedure, and most preferably while the heart remains beating.

A further aspect of the present invention provides a method for assessing blood flow in a portion of animal tissue wherein the tissue is a candidate for an invasive procedure, is being or has undergone an invasive procedure. In the latter case, an evaluation of the extent of blood flow through vasculature located downstream of a treated vessel assists a physician in assessing the success of the treatment. The method comprises identifying a portion of animal tissue; administering a fluorescent dye to the animal; obtaining at least one angiographic image of blood flowing through the tissue portion; and evaluating the at least one angiographic image to assess blood flow in the tissue portion.

This method may advantageously be used in the assessment of flow in coronary arteries and peripheral vasculature, and is preferably used during an invasive procedure. In one preferred aspect, the method contemplates obtaining an angiographic image of vasculature located downstream of a particular blood vessel, e.g., a coronary artery, that has undergone treatment, e.g., bypass, to assess the success of the bypass procedure. In another preferred aspect, the method contemplates obtaining an angiographic image of vasculature located downstream of a particular peripheral vessel that has undergone treatment, e.g., peripheral vessel bypass, wherein the image is obtained without incising the skin overlaying the downstream vasculature. In the latter aspect, the treated peripheral vessel and/or downstream vasculature is preferably located at a depth below the skin surface that permits the vasculature of interest to be assessed. Preferably, this depth is at least about 0.5 cm, and more preferably at least about 1 cm, below the skin surface.

This aspect of the present invention further contemplates assessing the blood flow in other body tissues including, but not limited to, muscle, stomach, liver, intestine, bladder, esophagus, lung, kidney and brain tissue. Angiographic images may be obtained beneath the surface of these tissues to a depth not exceeding that which permits the vasculature of interest to be evaluated. Again, and preferably, this depth is at least about 0.5 cm from the surface of any of the foregoing tissue, and more preferably at least about 1 cm, with access to the tissue by endoscope being a preferred route. This method may be used in connection with a variety of invasive procedures, such as those that assess whether internal bleeding has been halted. For example, a physician will be able to readily determine whether a surgical treatment successfully halted bleeding in what was previously a bleeding ulcer.

The inventive method further provides a means of evaluating various therapies, wherein the success of such therapies is indicated at least in part by the extent of blood flow in or about a particular tissue. The method contemplates obtaining a first angiographic image of a selected tissue; administering the therapy (e.g., a proposed therapeutic compound) to the animal; obtaining a second angiographic image of the same selected tissue at a later time (e.g., hours, days or months thereafter); and comparing first and second images to determine whether there is any change in vascular density and/or blood flow within the tissue. One use of this method is in the evaluation of angiogenic and anti-angiogenic agents, as well as in the research of such potential therapies. For example, an endoscope may be used to evaluate the impact, if any, of a particular therapy on decreasing the flow of blood into and/or through tumors, such as lung or colon tumors.

In another aspect of the present invention, a method of locating a blood vessel residing below the surface of vascularized tissue, e.g., a stenotic or occluded artery or vessels suitable for the creation of an AV fistula, is provided. The method comprises the steps of administering a fluorescent dye to an animal; obtaining at least one angiographic image of the vasculature located beneath the surface of the tissue; and examining the at least one angiographic image to locate at least one vessel residing beneath the surface of the tissue.

As the method permits ready visualization of vessels located down to at least about 0.5 cm, and preferably down to at least about 1 cm below the tissue surface, a physician is potentially able to complete a bypass or other coronary procedure involving the location of stenotic or occluded vessels residing below the tissue surface in less time, simply due to the time saved in locating the vessel to be treated.

In the context of renal failure, the method provides a means of locating arteries and veins that are suitable for the creation of an AV fistula, as well as providing information that assists a physician in determining which type of fistula to create based upon the structure of the vasculature. In a preferred aspect, the method permits angiographic images of peripheral vasculature located down to the previously-described depths to be obtained without requiring an incision into the skin to expose the vasculature of interest.

Angiographic images obtained in the absence of an incision may also be useful in assessing a peripheral (upper and lower extremities) vasculature bypass (by evaluating the blood flow through the vasculature downstream of the bypass), and in assessing endothelial dysfunction through the nail bed (by assessing the extent of blow flow through capillaries located under the nail bed).

The angiographic images obtained in accordance with the various aspects of the present invention depict the lumen (space) inside the arteries and veins located within the subject tissue. A relatively thick line indicates a major artery, whereas a relatively thin line indicates a smaller artery. A line of substantially uniform thickness indicates a vessel that is free of atherosclerotic plaques. In contrast, a line that is ragged, or that becomes thinner in certain sections, indicates the presence of stenosis, while a discontinuation of a line indicates the presence of an occlusion.

In yet another aspect, the present invention provides an apparatus and related method of providing images of high resolution that permit a physician to determine vessel diameters down to about 30 $\mu$m and less. This aspect of the invention will be discussed in more detail in subsequent paragraphs.

In order to obtain an image in accordance with the various aspects of the present invention, a fluorescent imaging agent is administered to the patient. The fluorescent agent should be selected so that when it passes through the vasculature of interest, at least one useful image of the vasculature can be obtained. Fluorescent dyes emit radiation of a known wavelength when excited by radiation of a particular wavelength. The radiation emitted by the excited dyes is detectable, and may be captured by a suitable device that converts the radiation into a viewable image.

While any fluorescent dye may be used that provides an image as described herein, indocyanine green (ICG) (IC-GREEN™, CARDIO-GREEN™, marketed by Akorn, Inc.), analogue members of the tricarbocyanine dyes, and mixtures thereof, are preferred. ICG is preferred because it is readily available, and has long been approved for administration to humans for ophthalmic angiography, cardiac output analysis and other indications.

The wavelengths for both absorption and emission radiation associated with such dyes are well known, and will not be repeated herein. By way of example, however, as the peak absorption and emission of ICG lies in the range of 800–850 nm, a radiation source emitting such wavelengths should be used to obtain one or more images of the vessels or tissue of interest.

Typically, the fluorescent agent is administered in a composition that includes a pharmaceutically acceptable carrier. The composition should be administered in an amount, and the fluorescent agent present at a concentration, sufficient to provide the degree of detail desired in the images. Advantageously, the agent is present in an amount of from about 1 to about 10 mg/ml, preferably from about 3 to about 7 mg/ml, and more preferably about 5 mg/ml of the composition, with the carrier constituting the balance thereof.

The carrier, which advantageously solvates but which may merely emulsify or suspend the agent, is provided to enhance the administration of the agent to a patient. Administration is typically accomplished via parenteral, IV injection, or other suitable means, with IV injection of the composition as a bolus being preferred, with the carrier being selected in view of the desired mode of administration.

Illustrative carriers that may be used include water, saline, alcohols, glycerin, polyethylene glycol, propylene glycol, polysorbate 80, Tweens, liposomes, amino acids, lecithin, dodecyl sulfate, lauryl sulfate, phospholipid, Cremophor, desoxycholate, soybean oil, vegetable oil, safflower oil, sesame oil, peanut oil, cottonseed oil, sorbitol, acacia, aluminum monstearate, polyoxyethylated fatty acids, povidone and mixtures thereof. Advantageously, the carrier comprises water and/or saline.

Optional components that may be present with the agent in the composition include tonicity and/or pH adjusters, e.g., NaOH, HCl, phosphate buffers, Tris buffer and the like.

The composition that comprises the agent may initially be provided in any suitable formulation, for example, as a lyophilizate for reconstitution before use, or as a liquid pre-mix, in a vial or syringe.

After administration of the imaging agent, a device capable of exciting any of the agent that may be present in the vasculature or tissue of interest, and a device capable of detecting the radiation emitted from any such agent, are activated. While each device may be provided in a separate housing, they may also be combined in a single housing without detracting from the present invention. Turning to FIG. 1, the device for exciting the agent advantageously comprises a laser 1 which emits radiation at a wavelength that causes any of the agent located within the vasculature or tissue of interest 3 irradiated thereby to emit radiation of a particular wavelength.

Lasers that are capable of providing radiation suitable to excite the agent sufficiently to permit detection of emissions are well known to those skilled in the art (e.g., Magnum 3000, Lasiris St-Laurent, Québec, Canada), and as such will not be described in detail herein. Generally, however, the devices comprise a laser driver and diode, and advantageously a bandpass filter 5. The filter 5 assists in optimizing image quality by ensuring that the radiation reaching the vessel is of a substantially uniform wavelength, i.e., the wavelength that causes the agent to fluoresce.

As the field of illumination provided by the laser alone is insufficient to radiate an anastomosis or other relatively large area, the laser advantageously includes optics 7 which diverge the laser light to cover the area of interest. By way of example, it has been found that optics that provide for even irradiation of a 7.5 cm×7.5 cm area will be sufficient to irradiate most anastomoses. Such optics are well known, and will therefore not be described in detail herein. Preferably, the optics should permit variation in the field of illumination, as it is sometimes desirable to concentrate the laser radiation on a relatively small area to enhance image resolution.

In a further optional enhancement, the laser output may be pulsed, synchronized with the camera image acquisition rate by use of a device such as a pulse generator 18. This reduces the amount of laser radiation received by the vessel or tissue while retaining image quality.

Devices capable of detecting emissions from imaging agents, and particularly the preferred fluorescent dyes, are also well known. Advantageously, a camera capable of obtaining multiple images over a period of time, such as a CCD camera 2 (e.g., Hitachi KP-M2, KP-M3), may be used to capture the emissions from the imaging agent. The camera selected, of course, should be one capable of capturing radiation of the wavelength emitted by the imaging agent. Preferably, the camera should capture such images at a rate of at least 15 images/sec, and more preferably at a rate of at least about 30 images/sec. The camera may also be fitted with a bandpass filter 6 to prevent capture of radiation other than that emitted by the imaging agent.

The camera focus may be by automatic or manual means. Further, and if desired, the camera may include a lens system 8 that enables an area of interest to be magnified. Preferably, the use of such a lens system is switched to the laser so that, when the lens system is engaged, the field of illumination provided by the laser is correspondingly reduced to match the field of view provided by the lens system. The result of this coordination is enhanced resolution. Polarizing filters 14a, 14b may also, if desired, be fitted to the laser and/or camera to enhance resolution.

Advantageously, a distance sensor 9 (e.g., WTA 24, Sick Optic-Electronic, Inc., Eden Prairie, Minn.) is included as part of the apparatus. This sensor, which preferably incorporates a visual display 9a, provides feedback to a physician so that the laser and camera can be located a distance from the vessel or tissue of interest that is optimal for the capture of high quality images, thereby minimizing the need for focusing of the camera during the procedure.

The relative positioning of the camera and laser can also affect image clarity, also referred to as visual noise. Preferably, and as shown in FIG. 1, the laser is located at an angle Θ of less than about 85°, and more preferably between about 20° and 70°, with respect to the axes of the laser and camera. Introducing the laser radiation into the body cavity at these angles reduces the amount of glare entering the camera arising from the liquid present in the cavity.

While the camera and laser may be located external to the patient, as shown in FIG. 1, it is also contemplated that at least one endoscope may be used to obtain images of the type described herein. For example, in this aspect of the invention, the endoscope would be inserted into the body, through an incision and/or body cavity, and positioned adjacent the area of interest A first instrument, typically a laser optic fiber, would be inserted into the endoscope, and used to provide radiation at an appropriate wavelength to cause any of a previously administered imaging agent within the subject vessel or tissue to emit detectable radiation. A second instrument inserted into the endoscope that would permit an image of the radiation-emitting agent within the vessel or tissue to be obtained. For example, an optical device connected to a CCD camera, such as those used to perform a colonoscopy, may be readily adapted for use in conjunction with the endoscopic procedure contemplated by the present invention. The manufacture of a suitable device in view of the disclosure provided herein is believed to be within the skill of the ordinary artisan, and will not be described in detail herein.

Preferably, the camera relays the captured images to an analog-to-digital converter 10 (typically a card located within PC 15), and then through image-capture and processing software running on a PC 15. A digital image of the fluorescing agent (which corresponds to the lumen of the vein, artery and/or anastomosis of interest) may then be displayed on a monitor 11, and recorded by the PC or a peripheral device in any suitable medium, e.g., hard drive, optical disc, magnetic tape, or the like. The camera may also direct images directly to a television 12/VCR 13 system, wherein the images may be displayed in real time and/or recorded for playback at a later time. Preferably, the monitor and/or television are located in the surgical suite, permitting real-time viewing of various aspects of the treated and surrounding vessels. A printer 16 may also be connected to the camera, PC and/or VCR to permit a hard copy of one or more angiographic images to be obtained.

Analog-to-digital converters are well known. These devices, as their name implies, convert the series of analog images captured by the camera to digital images. Image processing software is also well known, with a variety of software presently available that is capable of analyzing the treated and adjacent vessels.

In practice, it is preferred that the camera, laser and video monitor be located opposite the surgeon, to ensure that the surgeon has maximum space to position the device relative to the patient. The remaining components may be placed in any convenient location. Preferably, the laser, camera and/or video monitors are mounted on one or more armatures that provide freedom of movement along the x, y and z axes to provide maximum maneuverability, and which remain in a desired position after placement.

In a preferred aspect, the image-capture and processing software is able to provide a measurement of the diameter of a blood vessel, e.g., the diameter of the treated portion of a vessel and the end portions of the original vessel adjacent the treated portion. While a number of different methodologies may be used to provide this measurement, one such method follows. As the invention contemplates that the camera be positioned in a different location for each patient, or to obtain images of more than one vessel in a single patient, the software advantageously includes a calibration algorithm that permits an operator to assign a distance to a specified number of image pixels. While calibration can be completed using any suitable method, one method involves the use of a capillary tube of a known inner diameter filled with a fluorescent dye, e.g., ICG. The dye in the capillary tube is excited by radiation from a laser, and the resulting image of the fluorescing liquid detected by the camera, and processed by the software, is used to assign a length to the number of pixels that correspond to the inner diameter of the capillary tube.

The software preferably includes a further feature that selects the optimal images for analysis. The need to have such a feature is based upon the relatively fast flow of the imaging agent through the tissue or treated vessel of interest under normal conditions. Because the timing of the passage of imaging agent (if any is able to pass therethrough) through the tissue or vessel of interest cannot be precisely determined, there exist a number of leading and trailing images acquired before and after the images of interest. The software is preferably capable of determining the relative contrast of one image with another, and in this manner selects those frames with the greatest contrast for analysis, i.e., in the case wherein the agent is able to enter the vessel or tissue of interest, those frames in which the imaging agent is present therein and emitting detectable radiation. This selected series of images may then be analyzed to determine the diameter of the treated (or any other vessel) at a particular location, as well as the rate and volume of blood flow through the treated vessel and adjacent original vessel.

Software may also be used to compare images of pre- and post-treatment vessels to determine the relative flow rate of blood at or downstream of the treatment site. This comparison is accomplished by calculating and comparing the area of fluorescence (i.e., number of pixels associated with the fluorescing dye) in pre- and post-treatment images associated with a preselected section of the vessel, and/or comparing the relative average maximum fluorescent intensity of a preselected section of the vessel in each such image. A greater number of pixels, or greater average maximum fluorescent intensity, respectively, in the post-treatment images indicates improved blood flow in the preselected vessel section as a result of the treatment.

Similarly, the invention permits the diameter of a vessel to be calculated and compared both before and after stimulation, e.g., the administration of acetylcholine. This comparison is significant, because an increase in vessel diameter demonstrates that the vessel has maintained endothelial function, which is a positive indication of future vessel patency.

The advantages of the present invention are further illustrated by the following example. The particular details set forth therein should not be construed as a limitation on the claims of the present invention.

EXAMPLE

This example demonstrates the use of a preferred apparatus of the present invention in observing the flow of a fluorescent dye through a particular vessel, i.e., a mouse femoral artery, and langendorff perfused heart, and also demonstrates the ability of the apparatus to determine the diameter of a mouse femoral vessel under both normal conditions and under the influence of topically applied acetylcholine.

In this example, a fluorescent dye (ICG) was injected into the vascular bed (via jugular cannulation in the mouse: via an infusion line in the langendorff perfused heart) and excited using radiation from a laser source (806 nm). The fluorescence (radiation) emitted by the dye (830 nm) was captured as a series of angiograms using a CCD camera. The camera relayed the angiograms to analog-to-digital conversion software running on a PC that digitized the angiograms. The digitized images were then analyzed both qualitatively (by viewing the monitor) and quantitatively. One example of quantitative evaluation that was undertaken was the determination of the mouse femoral artery diameter using software comprising a sub-pixel edge detection system running on the PC.

The foregoing fluorescence imaging technique was used on the mouse femoral artery in vivo. A more detailed explanation of each component of the apparatus, preparation of the animal, injection of ICG, and analytical method, are set forth in the following paragraphs.

The laser device included an SDL-820 Laser Diode Driver (SDL Inc., San Jose, Calif.) that maintained a continuous wave output with an average current of 3.95 A, and an SDL-2382-P1 laser diode (SDL Inc.). The laser diode was used to illuminate the area of interest and excite the ICG dye, thereby inducing fluorescence in the region being imaged. A laser diode was used because, unlike an incandescent light source, a laser emits photons in a narrow frequency range, and thus eliminates the need for an excitation filter and the associated problem of heat dissipation. Because the laser-emitted wavelengths are limited, the excitation filter can be eliminated, improving the fluorescence. Consequently, a higher proportion of the light emitted from the laser diode is of the wavelength absorbed by ICG. It was found that use of an 800DF20 bandpass filter (Omega Optical Inc., Brattleboro, Vt.) in conjunction with the laser light source improved the results by selectively passing photons emitted at 806 nm (i.e., the wavelength at which ICG is excited).

The angiographic images were collected using a KP-160 video camera (Hitachi Denshi, Ltd., Tokyo, Japan). The KP-160 camera was selected because it is highly sensitive in the near-infrared region of the electromagnetic spectrum (which is also where ICG fluoresces), thus optimizing the capture of radiation emitted from the excited ICG. An 845DF25 bandpass filter (Omega Optical Inc., Brattleboro, Vt.) was coupled to the camera to exclude all photons that were not of the wavelength associated with ICG fluorescence. The laser diode was positioned at a 45° angle to the area of investigation in order to minimize specular reflectance (i.e., glare) arising from surface water from entering the camera. Glare is a major source of visual noise during imaging.

An analog-to-digital converter (752×480 pixel, 8-bit image processor, Model PIXCI-SV4, EPIX Inc., Buffalo Grove, Ill.) was employed to digitize the composite video signal output from the camera.

After each IV injection of an ICG dye bolus, a series of 264 interlaced images was collected at a rate of 30 per second.

The mouse was prepared by inducing anesthesia in an induction box using isoflurane (Ohmeda Pharmaceutical Products, Mississauga, ON, Canada) (4% in medical air, 4 L/min) and maintained by use of a facemask providing isoflurane at a rate of 1.5–2.0% in medical air (400 mL/min). During the experiment, the mouse was positioned on a thermostatted water blanket, with body temperature being monitored by a rectal temperature probe. To facilitate imaging of the vessels of interest, the thoracic, abdominal and inguinal areas of the mouse were shaved, the mouse positioned on its back, and the skin over the femoral vasculature was resected to expose the vasculature of interest. The jugular vein was cannulated using a piece of stretched PE10 tubing filled with saline containing 50 U heparin/mL.

After the mouse was prepared, a 10 $\mu$l bolus IV injection of ICG was administered, followed by an IV injection of 50 $\mu$l of saline solution. To prepare the bolus, 4 $\mu$g/ml of clinical grade ICG (CARDIO-GREEN™) was dissolved in sterile aqueous solvent within one hour of injection. All injections were administered via the cannula established in the jugular vein. The saline was used to flush the line and to ensure passage of an intact bolus through the femoral vasculature, producing a sharp wavefront.

Image analysis was performed using XCAP for Windows 95/98/NT version 1.0 (EPIX Inc., Buffalo Grove, Ill.). The image processing algorithm included the following steps.

1. Selection of vessels of interest. The anatomy of the vasculature varies between animals. Consequently, it was necessary to develop criteria for the selection of an area of interest. This process began with the positioning of the camera. The camera was positioned so that the field of view included the femoral artery and its branches. For the purposes of image analysis, the vessels of interest were the femoral artery and the branches that provided the highest resolution and the greatest degree of branching, usually tertiary or quaternary.

2. Calibration. The positioning of the camera with respect to the area being imaged varied with each animal, and it was therefore necessary to calibrate the camera for every image collected. A small diameter (320 $\mu$m) capillary tube (TSP320450; Polymicro Technologies, LLC, Phoenix, Ariz.) filled with ICG was used to calibrate the images. The image processing software includes a built-in calibration function that allows the specification of a set of pixel co-ordinates and the assignment of a user-defined value to the distance between these co-ordinates. The software's edge detector was used to determine the co-ordinates of the edges of the dye fluorescing in the capillary tube. The inner diameter of the capillary tube, in microns, was then assigned to the "length" of the distance between these points. Because this is a built-in feature of the software, all subsequent measurements in all frames of the image were stated in microns, rather than pixel units.

To avoid distortions due to camera movement or other stochastic phenomena, every image was calibrated. The advantages of this technique are that the same method was used to measure the calibration device as was used to measure the vessel, and the calibration device is measured in the same frame under the same optical conditions as the vessels.

3. Measurement of diameter using sub-pixel edger. All vessel diameters were measured using the built-in sub-pixel edger.

4. Selection of frames based on edge strength. Analysis of ICG images entails the selection of frames for analysis. The need to select frames is a consequence of the fast rate of ICG flow through the femoral artery with respect to the rate of image acquisition. This results in a leading and trailing sequence of frames that were acquired before and after ICG was detectable in the area being imaged. Edge strength, which is automatically calculated by the edge detector in our software, is a measure of the relative strength of the edge, i.e., the ratio of the value of the pixels on one side of the edge to the value of those on the other side. The ratio is highest when the contrast is greatest, which corresponds to the greatest intensity of ICG fluorescence. The vessels that were measured have two edges, thus ten frames in which the product of the edge strengths was the greatest were selected for analysis.

After the foregoing was completed, the vessel diameters and standard errors were calculated as described above. Student's t-test for paired values was applied to determine the statistical significance between the measurements (border of significance, p=0.01.)

Preliminary data on the effects of different size vessels in the mouse (femoral artery) are given in the Table. The data confirms the ability to monitor changes in small vessels (e.g., 58 microns) when even a low concentration of acetylcholine (0.01 $\mu$M) is applied.

TABLE

Effects of Acetylcholine

| Acetylcholine concentration | Vessel Diameter (microns) | | | | |
|---|---|---|---|---|---|
| | control | 0.01 $\mu$M | .01 $\mu$M | 1.0 $\mu$M | 10.0 $\mu$M |
| Primary | 92.7 ± 1.2 | 58.2 ± 1.3 | 61.5 ± 1.7 | 58.3 ± 1.5 | 64.6 ± 1.5 |
| Secondary | 69.4 ± 0.3 | 67.0 ± 1.3 | 75.1 ± 1.2 | 90.0 ± 1.8 | 75.0 ± 1.4 |
| Tertiary | 57.5 ± 0.7 | 42.9 ± 0.6 | 44.9 ± 0.6 | 47.1 ± 1.2 | 42.9 ± 0.8 |

$p < 0.05$

The foregoing demonstrates the ability of the present invention to observe the flow of blood through a vessel, to determine the diameter of a vessel, and to monitor changes in the reactivity of a vessel after the administration of acetylcholine.

All of the references cited herein, including patents, patent applications, and publications, are hereby incorporated in their entireties by reference. Further, and unless otherwise indicated, references to a single component, structure or step herein should be construed as also including more than one such component, structure or step, i.e., at least one or one or more.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for visualizing, during an invasive surgical procedure on an animal, at least a portion of at least one blood vessel of the animal that is exposed by the procedure, the method comprising:

(a) administering a fluorescent dye to the animal;
   (b) obtaining at least one angiographic image of the at least one blood vessel portion; and
   (c) evaluating the at least one anglographic image to determine patency of the at least one blood vessel portion.

wherein the at least one blood vessel is a coronary artery,
   wherein the at least one blood vessel portion is a bypass graft.

2. The method of claim 1, wherein step (b) is performed while the animal's heart is beating.

3. The method of claim 1, wherein a plurality of images of the vessel portion are obtained during the invasive procedure in which the bypass graft is created in the vessel portion, and wherein a first angiographic image of the vessel portion is obtained prior to creation of the bypass graft and a second anglographic image of the vessel portion is obtained after the bypass graft is created.

4. The method of claim 3, wherein the first and second anglographic images are obtained while the heart is beating.

5. The method of claim 1, wherein the fluorescent dye is selected from the group consisting of tricarbocyanine dyes, and mixtures thereof.

6. The method of claim 5, wherein the fluorescent dye is ICG.

7. The method of claim 1, wherein a plurality of angiographic images is obtained during step (b).

8. The method of claim 7 further comprising displaying the plurality of angiographic images on a video monitor.

9. The method according to claim 8, wherein the plurality of angiographic images is obtained using a CCD camera.

10. The method of claim 9 further comprising storing the plurality of anglographic images on a recordable medium.

11. The method according to claim 10, wherein the plurality of images is obtained at least in part using an endoscope.

* * * * *